United States Patent [19]

Desbois

[11] 4,446,078

[45] May 1, 1984

[54] PROCESS FOR THE PREPARATION OF α,α-DIFLUOROALKYL-THIOPHENYL KETONES

[75] Inventor: Michel Desbois, Rillieux, France

[73] Assignee: Rhone-Poulenc Specialites Chimiques, Courbevoie, France

[21] Appl. No.: 393,121

[22] Filed: Jun. 28, 1982

[30] Foreign Application Priority Data

Jan. 21, 1982 [FR] France .................... 82 00876

[51] Int. Cl.$^3$ .................... C07C 121/75; C07C 45/45; C07C 149/30
[52] U.S. Cl. .................... 260/465 F; 260/465 D; 260/465 E; 260/465 G; 562/432; 562/436; 562/459; 562/460; 564/329; 568/43; 568/306; 568/314; 568/315; 568/319; 568/322
[58] Field of Search .......... 260/465 F, 465 G, 465 D, 260/465 E; 568/43, 306, 314, 315, 316, 319, 322, 323; 562/432, 436, 459, 460; 564/329

[56] References Cited

U.S. PATENT DOCUMENTS

| | | | |
|---|---|---|---|
| T970,006 | 5/1978 | Rose | 260/591 |
| 2,273,922 | 2/1942 | Benning | 260/649 |
| 2,275,312 | 3/1942 | Tinker | 260/515 |
| 2,372,562 | 8/1942 | Emerson | 260/592 |
| 2,735,868 | 2/1956 | Frevel et al. | 260/592 |
| 2,781,402 | 2/1957 | Chadwick | 260/607 |
| 2,974,172 | 3/1961 | Luvisi | 260/592 |
| 3,187,057 | 6/1965 | Peter et al. | 260/651 |
| 3,387,035 | 6/1968 | Gray et al. | 260/591 |
| 3,732,307 | 5/1973 | Middleton | 260/566 B |
| 3,883,594 | 5/1975 | Schmerling | 260/592 |
| 3,953,400 | 4/1976 | Dahl | 260/47 R |
| 4,178,460 | 12/1979 | Berkelhammer et al. | 260/465 F X |
| 4,207,266 | 6/1980 | Opie | 260/651 F |
| 4,276,226 | 6/1981 | Clement et al. | 260/410.5 |

FOREIGN PATENT DOCUMENTS

| | | |
|---|---|---|
| 43861 | 1/1981 | European Pat. Off. . |
| 876690 | 5/1953 | Fed. Rep. of Germany . |
| 1645153 | 10/1970 | Fed. Rep. of Germany . |
| 2451037 | 4/1976 | Fed. Rep. of Germany . |
| 1567806 | 4/1969 | France . |
| 2357517 | 2/1978 | France . |
| 135756 | 10/1979 | Japan . |
| 1164817 | 9/1969 | United Kingdom . |
| 2030158 | 4/1980 | United Kingdom . |
| 2045760 | 11/1980 | United Kingdom . |

OTHER PUBLICATIONS

Patai, The Chemistry of the Carbonyl Group, John Wiley & Sons, New York, pp. 236–237 (1966).
Correlation Analysis in Chemistry, Plenum Press, ed. Chapman et al., Table 10.1 (1978).
L. Yagupolskii et al., Chem. Abstracts 61:8217 (1964).
V Boiko et al., Chem. Abstracts 87:134226h (1977).
Hansch et al., Journal of Medicinal Chemistry, vol. 16, No. 11, p. 1207 (1973).
Olar, Friedel–Crafts and Related Reactions III, Part I, Interscience Publishers, pp. 8–382 (1964).
Buu-Hoi et al., J. Org. Chem., vol. 26, 2401-2 (1961).

Primary Examiner—Dolph H. Torrence

[57] ABSTRACT

A process for the preparation of α,α-difluoroalkoxy or α,α-difluoroalkylthiophenyl ketones, in which a polyhaloalkoxybenzene or a polyhaloalkylthiobenzene is reacted with a carboxylic acid, a precursor or a derivative of this acid in the presence of boron trifluoride in such an amount that the absolute pressure of the boron trifluoride within the reaction vessel exceeds 1 bar, and in the presence of hydrofluoric acid as a solvent. The resultant products are useful as intermediates in the synthesis of compounds having phytosanitary (e.g., herbicidal) or pharmaceutical activity.

9 Claims, No Drawings

PROCESS FOR THE PREPARATION OF α,α-DIFLUOROALKYL-THIOPHENYL KETONES

The instant invention is directed to a process for the preparation of α, α-difluoroalkoxy or α, α-difluoroalkylthiophenyl ketones.

Various methods for the preparation of compounds of this type are already known in the art. For example, French patent application No. 2,272,079 described in particular the preparation of isopropyl p-trifluoromethoxyphenyl ketone. A Grignard reagent is prepared from p-bromophenyl oxide and trifluoromethane and magnesium, which is reacted with isobutyronitrile at reflux. The product is hydrolyzed to yield the desired ketone. French patent application No. 2,194,422 discloses a similar process.

This type of process has serious drawbacks which make it unattractive on an industrial scale. There are numerous stages and the reaction times are long. Moreover, the yields are unsatisfactory, as they only reach 30 to 40%. In addition, and this is certainly not the least important factor, the use of organomagnesium compounds and of the solvents required for use therewith is hazardous to the environment: it is necessary to take precautions for industrial production, which increases the cost of the process.

Also known are methods for the acylation of aromatic substrates (other than trifluoromethoxybenzenes or trifluoromethylthiobenzenes) in the presence of Friedel-Crafts catalysts such as $AlCl_3$ (see, for example, Olah, *Friedel-Crafts and Related Reactions* III, Part I, Interscience Publishers, p. 8 et seq. (1964)). Experiments have shown that Friedel-Crafts catalysts, such as $AlCl_3$, are ineffective when the aromatic compound bears an $OCF_3$ or $SCF_3$ group; in fact, there is even degradation of these groups. In the presence of sulfuric acid, another classic catalyst, the $OCF_3$ and $SCF_3$ groups are similarly degraded.

The operating conditions have now been determined which make it possible to carry out the acylation reaction on aromatic substrates having a polyhaloalkoxy, in particular trihalomethoxy, or polyhaloalkylthio, in particular trihalomethylthio, substituent, which could not be achieved according to the prior art.

The instant invention is directed to a process for the preparation of α, α-difluoroalkoxy or α, α-difluoroalkylthiophenyl ketones, characterized in that a polyhaloalkoxybenzene or a polyhaloalkylthiobenzene is reacted with a carboxylic acid, a precursor or a derivative thereof in the presence of boron trifluoride in an amount such that the absolute pressure of the boron trifluoride in the reaction vessel exceeds 1 bar, and in the presence of hydrofluoric acid as a solvent.

Buu-Hoi and Xuong have described the synthesis of phenol ketones derived from di- and triphenols and from α-and β-naphthol by condensation of carboxylic acids with the phenols in the presence of the gas generated by reaction of oleum with potassium fluoroborate (*Journal of Organic Chemistry* 26, 2401–02 (July 1961)). This gas contains boron trifluoride and hydrofluoric acid, in addition to other compounds, such as primarily fluorosulfonic acid. According to this article, the hydrofluoric acid enhances the condensation-promoting properties of the boron trifluoride.

It should be noted that the reaction described in this article is carried out in a solvent medium, such as xylene. It should also be noted that the aromatic compound which is condensed with the carboxylic acid is a phenol, which is a benzene bearing an activating substituent (OH). This process cannot be directly employed for the preparation of α, α-difluoroalkoxy or α, α-difluoroalkylthiophenyl ketones; the solvent would react with he carboxylic acid, its precursor or its derivative, because polyhaloalkoxy or polyhaloalkylthiobenzenes are less reactive than xylene.

Moreover, the gas generated in the reaction of oleum and potassium fluoroborate cannot be likened to the boron trifluoride/hydrofluoric acid pair used according to the inventive process. According to the invention, hydrofluoric acid in the liquid state acts as a solvent, whereas, according to the process of the above-noted article, it is in the gas phase.

Within the scope of this invention, the terms polyhaloalkoxybenzene and polyhaloalkylthiobenzene refer both to the compounds themselves and to analogues thereof with one or a plurality of substituents on the benzene nucleus.

More particularly, the polyhaloalkoxybenzenes or polyhaloalkylthiobenzenes embraced by this invention have the general formula:

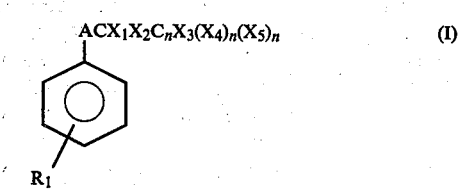

$$ACX_1X_2C_nX_3(X_4)_n(X_5)_n \qquad (I)$$

wherein $X_1$ and $X_2$ are identical or different and represent Cl, Br, I, or F; $X_3$, $X_4$ and $X_5$ are identical or different and represent H, Cl, Br, I or F; n is zero or an integer equal to or less than 5 ($0 \leq n \leq 5$); A represents O or S; and $R_1$ represents at least one element or moiety selected from hydrogen OH, Cl, Br, I, F, alkyl and alkoxy radicals having from 1 to 6 carbon atoms, and phenyl and phenoxy radicals substituted by at least one group more deactivating than a $ACX_1X_2C_nX_3(X_4)_n(X_5)_n$ group.

The phenyl and phenoxy radicals $R_1$ must be substituted by groups more deactivating than the $ACX_1X_2C_nX_3(X_4)_n(X_5)_n$ group so that the acylation reaction takes place on the benzene nucleus carrying the $ACX_1X_2C_nX_3(X_4)_n(X_5)_n$ group. Otherwise, acylation would occur on the phenyl or phenoxy radical. Examples of groups more deactivating than $ACX_1X_2C_nX_3(X_4)_n(X_5)_n$ group includes COOH, CN, $NO_2$, $CX_1X_2X_3$ groups and keto groups.

The compounds of Formula I in which n=0 or 1 and $X_1$, $X_2$ and $X_3$ are identical are of particular interest in the present invention. Among these, compounds in which $X_1$, $X_2$ and $X_3$ represent fluorine are preferred.

One can cite as examples of compounds of Formula I the following: trifluoromethoxybenzene; trifluoromethylthiobenzene; o-, m- and p-chlorotrifluoromethoxybenzene; o-, m-and p-chlorotrifluoromethylthiobenzene; o-, m- and p-bromotrifluoromethylthiobenzene; o-, m- and p-bromotrifluoromethoxybenzene; o-, m- and p-methyltrifluoromethoxybenzene; o-, m- and p-methyltrifluoromethylthiobenzene; o-, m- and p-methoxytrifluoromethoxybenzene; o-, m- and p-methoxytrifluoromethylthiobenzene; o-, m- and p-hydroxytrifluoromethoxybenzene; o-, m- and p-hydroxytrifluoromethylthiobenzene; 4-trifluoromethyl-4'-trifluoromethoxybiphenyl; and 3-nitro-4'-trifluoromethoxydiphenyl oxide (as well as the chlorinated, brominated, or iodinated analogues of the above compounds); difluorobromomethoxybenzene; difluorobromomethylthiobenzene; dichlorofluoromethoxybenzene; dichlorofluoromethylthiobenzene; difluorochloromethoxybenzene; difluorochloromethylthiobenzene; $\alpha,\alpha,\beta,\beta,\beta$-pentachloroethoxybenzene; $\alpha,\alpha,\beta,\beta,\beta$-pentachloroethylthiobenzene; difluoromethoxybenzene; difluoromethylthiobenzene; $\alpha,\alpha,\beta,\beta$-tetrafluoroethoxybenzene; $\alpha,\alpha,\beta,\beta$-tetrafluoroethylthiobenzene; $\alpha,\alpha,\beta,\beta$-tetrafluoro-$\beta$-bromoethoxybenzene; $\alpha,\alpha,\beta,\beta$-tetrafluoro-$\beta$-bromoethylthiobenzene; and $\alpha,\alpha$-difluoro-$\beta,\beta,\beta$-trichloroethoxybenzene.

Within the scope of this invention, the terms carboxylic acid, precursors and derivatives thereof refer to all the acylation reagents well known in the prior art.

According to a particular embodiment of the invention, the carboxylic acid, its precursor or derivative are of the general formula:

$$R_2COX_6 \qquad (II)$$

wherein $R_2$ represents an aliphatic or aromatic radical and $X_6$ represents halogen, a group derived from the anion of an inorganic acid, OH, $OR_3$, $OCOR_4$, $NH_2$, $NHR_5$, or $NR_6R_7$, wherein each of $R_3$, $R_4$, $R_5$, $R_6$, and $R_7$ is an aromatic or aliphatic radical. $ClO_4^-$ and $BF_4^-$ are examples of groups derived from the anion of an inorganic acid.

The invention is well suited in particular to the use of a compound of Formula II wherein $R_2$ represents an alkyl, phenyl, alkylphenyl or phenylalkyl radical or a phenyl radical bearing at least one substituent such as, for instance, halogen, $NO_2$, CN, $NH_2$ or COOH.

Examples of such compounds include acetyle chloride acetic acid, acetic anhydride, benzoyl chloride, benzoic acid, benzoic anhydride, orthochlorobenzoyl chloride, parachlorobenzoyl chloride, parafluorobenzoyl chloride, paratrifluoromethylbenzoyl fluoride, orthotrifluoromethylbenzoyl fluoride, paranitrobenzoyl chloride, paranitrobenzoic acid, paraaminobenzoic acid, isobutyroyl chloride, isobutyric acid, propanoic acid, propanoyl chloride, paratoluyl chloride and parabenzylbenzoyl chloride.

The process according to the invention is preferably carried out by using an amount of hydrofluoric acid such that the molar ratio of the hydrofluoric acid to the compound of Formula I is between 5 and 50. Even more preferably, this ratio is between 10 and 30.

The hydrofluoric acid used is preferably anhydrous. The use of an aqueous hydrofluoric acid would result in a useless consumption of boron trifluoride in the form of a complex of HF, $BF_3$ and $H_2O$ ($H_3O^+BF_4^-$).

The compounds of Formulas I and II are used in substantially equimolar amounts. A slight excess of the compound of Formula I may, however, be desirable.

More particularly, it is preferred to use an amount of boron trifluoride such that the absolute pressure of $BF_3$ within the reaction enclosure is between 6 and 20 bars. The more the pressure is increased, the greater the increase in the rate of reaction. A pressure in excess of 20 bars is not excluded from the scope of the invention but it does not provide any particular benefit. The pressure will therefore be adjusted to maximize the efficiency of the process.

The process according to the invention is preferably carried out at a temperature between $-20°$ C. and 150° C. The reaction times are generally between a few minutes and several hours.

The $\alpha,\alpha$-difluoroalkoxy or $\alpha,\alpha$-difluoroalkylthiophenyl ketones obtained according to the process of the invention have the general formula:

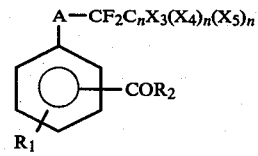

wherein A, $R_1$, $R_2$, $X_3$, $X_4$, $X_5$ and n have the same meaning as above.

Upon completion of the reaction, which is performed in a HF medium, the resultant compound will bear a substituent $ACF_3$ when, in the compound of Formula I, n= and $X_3$ is a halogen. $ACCl_3$, $ACBr_3$, $ACI_3$, $ACF_2Br$, $ACCl_2F$, $ACF_2Cl$, etc., are transformed under the reaction conditions into $ACF_3$ groups. When n=0 and $X_3$ is hydrogen, the resultant compound will bear a substituent $ACF_2H$. When n is greater than zero, only the substituents $X_1$ and $X_2$, when they are not originally fluorine, will be exchanged therefor.

The position of the $COR_2$ group with respect to the $ACF_2C_nX_3(X_4)_n(X_5)_n$ and $R_1$ groups is in conformity with the substitution rules well known to the organic chemist.

The ketones produced by the process of the invention are useful, in particular, as intermediates in the synthesis of compounds having a pharmaceutical or phytosanitary (e.g., herbicidal) activity.

The following are examples of compounds that can be prepared by the process of the invention: 4-trifluoromethoxy-2'-chlorobenzophenone; 4-trifluoromethoxy-4'-chlorobenzophenone; 4-trifluoromethoxybenzophenone; 4-trifluoromethoxyacetophenone; 4-trifluoromethoxyisobutyrophenone; 4-trifluoromethoxy-4'-fluorobenzophenone; 4-trifluoromethoxy-4'-trifluoromethylbenzophenone; 4-trifluoromethoxy-2'-trifluoromethylbenzophenone; 4-trifluoromethoxy-2-chloro-4'-nitrobenzophenone; 2-trifluoromethoxy-5-methyl-4'-aminobenzophenone; 2-trifluoromethoxy-4-chloro-4'-flurobenzophenone; 3-trifluoromethoxy-4-hydroxy-3'-cyanobenzophenone; 3-trifluoromethoxy-4',6-dichlorobenzophenone; 2-trifluoromethoxy-4',5-dichlorobenzophenone; 4-difluoromethoxy-4'-fluorobenzophenone; 4-($\alpha,\alpha$-difluoro-$\beta,\beta,\beta$-trichloroethoxy)-4'-chlorobenzophenone; 4-($\alpha,\alpha,\beta,\beta$-tetrafluoroethoxy)-'-fluorobenzophenone and 4-($\alpha,\alpha,\beta,\beta$-tetrafluoro-$\beta$-bromoethoxy)-2'-fluorobenzophenone, as well as the sulfur analogues of the above compounds.

In order to disclose more clearly the nature of the present invention, the following examples illustrating specific embodiments of the invention are given. It should be understood, however, that this is done solely by way of example and is intended neither to delineate the scope of the invention nor limit the ambit of the appended claims.

EXAMPLE 1

Into a 250 ml stainless steel reactor equipped with a magnetic stirrer system, 100 ml of anhydrous HF, 23.6 g (0.3 mole) of acetyl chloride, and 32.4 g (0.2 mole) of trifluoromethoxybenzene were introduced at around 0° C. The reactor was closed and gaseous boron trifluoride (BF$_3$) introduced until a constant pressure of 6 bars was achieved. The reaction was then allowed to proceed with stirring at ambient temperature for 3 hours. Following reaction, the reactor was decompressed to atmospheric pressure, then the reaction mixture poured over 200 g of crushed ice. The resultant heterogeneous mixture was extracted three times with 200 ml of methylene chloride. The organic phases were washed three times with 200 ml of water, once with 200 ml of 3% aqueous potassium hydroxide solution, and twice with 200 ml of water. The organic phase was dried over magnesium sulfate and the solvent eliminated by distillation under reduced pressure. 37.2 g (yield: 91%) of p-trifluoromethoxyacetophenone having a purity of 96.3% was recovered.

EXAMPLE 2

The procedure of Example 1 was followed with the following compounds and under the following conditions:

| Anhydrous hydrofluoric acid | 100 g |
|---|---|
| Trifluoromethoxybenzene | 32.4 g (0.2 mole) |
| Orthochlorobenzoyl chloride | 35 g (0.2 mole) |
| Boron trifluoride | 6 bars at 20° C. |
| Temperature | 20° C. |
| Duration | 1 hour |

53.3 g (yield: 88.7%) of liquid 4-trifluoromethoxy2'-chlorobenzophenone having a purity of 95.5% was recovered.

EXAMPLE 3

The procedure of Example 1 was followed with the following compounds and under the following conditions:

| Anhydrous hydrofluoric acid | 100 g |
|---|---|
| Trifluoromethoxybenzene | 32.4 g (0.2 mole) |
| Isobutyroyl chloride | 23 g (0.216 mole) |
| Boron trifluoride | 10 bars at 20° C. |
| Temperature | 20° C. |
| Duration | 20 hours |

27.8 g (yield: 60%) of liquid p-trifluoromethoxyisobutyrophenone having a purity of 70% was recovered. A simple distillation allowed for recovery of 17 g of p-trifluoromethoxyisobutyrophenone having a purity of 99.5% (boiling point: 105° C. at 10 mm mercury).

EXAMPLE 4

The procedure of Example 1 was followed with the following compounds and under the following conditions:

| Anhydrous hydrofluoric acid | 100 g |
|---|---|
| Trifluoromethoxybenzene | 32.4 g (0.2 mole) |
| p-chlorobenzoyl chloride | 35 g (0.2 mole) |
| Boron trifluoride | 10 bars at 20° C. |
| Temperature | 5° C. |
| Duration | 3 hours |

55.1 g (yield: 91.7%) of 4-trifluoromethoxy-4'chlorobenzophenone having a purity of 98.2% was recovered. Melting point: 74.5°–75° C. (MeOH).

EXAMPLE 5

The procedure of Example 1 was followed with the following compounds and under the following conditions:

| Anhydrous hydrofluoric acid | 100 g |
|---|---|
| Trifluoromethoxybenzene | 32.4 g (0.2 mole) |
| p-fluorobenzoyl chloride | 31.7 g (0.2 mole) |
| Boron trifluoride | 8 bars at 20° C. |
| Temperature | 20° C. |
| Duration | 24 hours |

52.2 g (yield: 92%) of 4-trifluoromethoxy-4'-fluorobenzophenone having a purity of 99% was recovered. Melting point: 42°–43° C. (MeOH).

EXAMPLE 6

The procedure of Example 1 was followed with the following compounds and under the following conditions:

| Anhydrous hydrofluoric acid | 100 g |
|---|---|
| Trifluoromethoxybenzene | 32.4 g (0.2 mole) |
| Benzoic anhydride | 22.6 g (0.1 mole) |
| Boron trifluoride | 10 bars at 20° C. |
| Temperature | 40° C. |
| Duration | 2 hours |

45.8 g (yield: 86%) of 4-trifluoromethoxybenzophenone having a purity of 95% was recovered.

EXAMPLE 7

The procedure of Example 1 was followed with the following compounds and under the following conditions:

| Anhydrous hydrofluoric acid | 100 g |
|---|---|
| Trifluoromethoxybenzene | 32.4 g (0.2 mole) |
| Benzoic acid | 24.4 g (0.2 mole) |
| Boron trifluoride | 10 bars at 20° C. |
| Temperature | 50° C. |
| Duration | 3 hours |

40.3 g (yield: 75.7%) of 4-trifluoromethoxybenzophenone having a purity of 96% was recovered.

EXAMPLE 8

The procedure of Example 1 was followed with the following compounds and under the following conditions:

| Anhydrous hydrofluoric acid | 100 g |
|---|---|
| Trifluoromethoxybenzene | 32.4 g (0.2 mole) |
| p-trifluoromethylbenzoyl fluoride | 38.4 g (0.2 mole) |
| Boron trifluoride | 6 bars at 20° C. |
| Temperature | 30° C. |
| Duration | 1 hour |

48 g (yield: 71.8%) of 4-trifluoromethyl-4'-trifluoromethoxybenzophenone having a purity of 99.2% was recovered. Melting point: 61.5°–62° C. (MeOH).

EXAMPLE 9

The procedure of Example 1 was followed with the following compounds and under the following conditions:

| Anhydrous hydrofluoric acid | 100 g |
|---|---|
| Trifluoromethoxybenzene | 32.4 g (0.2 mole) |
| o-trifluoromethylbenzoyl fluoride | 38.4 g (0.2 mole) |
| Boron trifluoride | 6 bars at 20° C. |
| Temperature | 30° C. |
| Duration | 2 hours |

61 g (yield: 91.3%) of liquid 2-trifluoromethyl-4'-trifluoromethoxybenzophenone having a purity of 95% was recovered.

EXAMPLE 10

The procedure of Example 1 was followed with the following compounds and under the following conditions:

| Anhydrous hydrofluoric acid | 130 g |
|---|---|
| Trifluoromethoxybenzene | 32.4 g (0.2 mole) |
| Isobutyroyl chloride | 23.5 g (0.22 mole) |
| Boron trifluoride | 23 bars at 0° C. |
| Temperature | −10° C. |
| Duration | 18 hours |

38.5 g (yield: 90%) of p-trifluoromethoxyisobutyrophenone having a purity of 96% was recovered.

EXAMPLE 11

The procedure of Example 1 was followed (using a 1e reactor) with the following compounds and under the following conditions:

| Anhydrous hydrofluoric acid | 300 g |
|---|---|
| Trifluoromethoxybenzene | 97.2 g (0.6 mole) |
| Isobutyroyl chloride | 64 g (0.6 mole) |
| Boron trifluoride | 15 bars at −15° C. |
| Temperature | −15° C. |
| Duration | 18 hours |

102.6 g (yield: 80%) of p-trifluoromethoxyisobutyrophenone having a purity of 95% was recovered. In this example, the HF solvent was eliminated by distillation under reduced pressure (100 mm of Hg) at 15° C.

EXAMPLE 12

The procedure of Example 1 was followed with the following compounds and under the following conditions:

| Anhydrous hydrofluoric acid | 100 g |
|---|---|
| Trifluoromethylthiobenzene | 17.8 g (0.1 mole) |
| p-fluorobenzoyl chloride | 15.8 g (0.1 mole) |
| Boron trifluoride | 10 bars at 20° C. |
| Temperature | 20° C. |
| Duration | 4 hours |

27 g (yield: 92%) of 4-trifluoromethylthio-4'-fluorobenzophenone having a purity of 93% was recovered.

EXAMPLE 13

The procedure of Example 1 was followed with the following compounds and under the following conditions:

| Anhydrous hydrofluoric acid | 100 g |
|---|---|
| Trichloromethoxybenzene | 42.3 g (0.2 mole) |
| p-fluorobenzoyl chloride | 31.7 g (0.2 mole) |
| Boron trifluoride | 10 bars at 20° C. |
| Temperature | 50° C. |
| Duration | 2 hours |

50.2 g (yield: 88.5%) of 4-trifluoromethoxy-4'-fluorobenzophenone having a purity of 94% was recovered. During the course of the reaction, a marked increase in pressure due to the generation of hydrochloric acid originating from the Cl-F exchange was observed.

EXAMPLE 14

The procedure of Example 1 was followed with the following compounds and under the following conditions:

| Anhydrous hydrofluoric acid | 100 g |
|---|---|
| Difluorobromomethoxybenzene | 44.6 g (0.2 mole) |
| p-chlorobenzoyl chloride | 35 g (0.2 mole) |
| Boron trifluoride | 10 bars at 20° C. |
| Temperature | 20° C. |
| Duration | 3 hours |

53 g (yield: 85%) of 4-trifluoromethoxy-4'-chlorobenzophenone having a purity of 94% was recovered. During the course of the reaction, an increase in pressure due to the generation of hydrobromic acid resulting form the Br-F exchange was observed.

EXAMPLE 15

The procedure of Example 1 was followed with the following compounds and under the following conditions:

| Anhydrous hydrofluoric acid | 100 g |
|---|---|
| Trichloromethylthiobenzene | 22.7 g (0.1 mole) |
| p-fluorobenzoyl chloride | 15.8 g (0.1 mole) |
| Boron trifluoride | 15 bars at 20° C. |
| Temperature | 50° C. |
| Duration | 8 hours |

25 g (yield: 85%) of 4-trifluoromethylthio-4'-fluorobenzophenone having a purity of 91% was recovered. During the course of the reaction, an increase in pressure due to the generation of hydrochloric acid resulting from the Cl-F exchange was observed.

EXAMPLE 16

The procedure of Example 1 was followed with the following compounds and under the following conditions:

| Anhydrous hydrofluoric acid | 100 g |
|---|---|
| p-chlorotrifluoromethoxybenzene | 19.7 g (0.1 mole) |
| p-chlorobenzoyl chloride | 17.5 g (0.1 mole) |
| Boron trifluoride | 6 bars at 20° C. |
| Temperature | 120° C. |
| Duration | 18 hours |

8.7 g (yield: 26%) of a crude mixture of 3-trifluoromethoxy-4',6-dichlorobenzophenone and 2-trifluoromethoxy-4',5-dichlorobenzophenone was recovered.

EXAMPLE 17

The procedure of Example 1 was followed with the following compounds and under the following conditions:

| Anhydrous hydrofluoric acid | 100 g |
|---|---|
| α,α-difluoromethoxybenzene | 28.8 g (0.2 mole) |
| p-fluorobenzoyl chloride | 31.7 g (0.2 mole) |
| Boron trifluoride | 10 bars at 20° C. |
| Temperature | 30° C. |
| Duration | 3 hours |

45.5 g (yield: 85%) of crude 4-difluoromethoxy-4'fluorobenzophenone was recovered.

EXAMPLE 18

The procedure of Example 1 was followed with the following compounds and under the following conditions:

| Anhydrous hydrofluoric acid | 50 g |
|---|---|
| α,α,β,β,β-pentachloroethoxybenzene | 5 g (0.017 mole) |
| p-chlorobenzoyl chloride | 3 g (0.017 mole) |
| Boron trifluoride | 6 bars at 20° C. |
| Temperature | 20° C. |
| Duration | 4 hours |

6 g (yield: 88%) of crude 4-($\alpha,\alpha$-difluoro-$\beta,\beta,\beta$-trichloroethoxy)-4'-chlorobenzophenone was recovered.

EXAMPLE 19

The procedure of Example 1 was followed with the following compounds and under the following conditions:

| Anhydrous hydrofluoric acid | 20 g |
|---|---|
| α,α,β,β-tetrafluoroethylthiobenzene | 1 g (0.005 mole) |
| p-fluorobenzoyl chloride | 0.7 g (0.005 mole) |
| Boron trifluoride | 12 bars at 20° C. |
| Temperature | 0° C. |
| Duration | 3 hours |

1.2 g (yield: 72%) of crude 4-($\alpha,\alpha,\beta,\beta$-tetrafluoroethylthio)-4'-fluorobenzophenone was recovered.

EXAMPLE 20

The procedure of Example 1 was followed with the following compounds and under the following conditions:

| Anhydrous hydrofluoric acid | 30 g |
|---|---|
| α,α,β,β-tetrafluoro-β-bromoethylthiobenzene | 2 g (0.007 mole) |
| o-fluorobenzoyl chloride | 1.5 g (0.009 mole) |
| Boron trifluoride | 12 bars at 20° C. |
| Temperature | 0° C. |
| Duration | 4 hours |

2.1 g (yield: 75%) of crude 4-($\alpha,\alpha,\beta,\beta$-tetrafluoro-$\beta$-bromoethylthio)-2'-fluorobenzophenone was recovered.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed.

I claim:

1. A process for the preparation of $\alpha,\alpha$-di-fluoroalkoxy or $\alpha,\alpha$-difluoroalkylthiophenyl ketones having the formula:

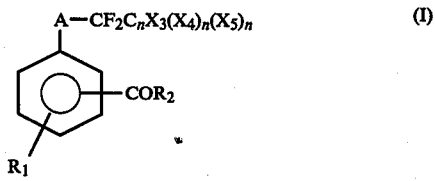

said process comprising reacting a polyhaloalkoxybenzene or a polyhaloalkylthiobenzene having the formula:

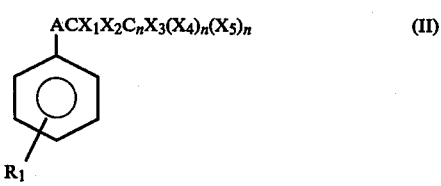

in a reaction vessel with a carboxylic acid, a derivative, or a precursor thereof having the formula:

$$R_2COX_6 \qquad (III)$$

in the presence of boron trifluoride in an amount such that the absolute pressure of the boron trifluoride within the reaction vessel exceeds 1 bar, and in the presence of hydrofluoric acid as a solvent;
wherein A represents O or S;

$X_1$ and $X_2$ are identical or different and represent Cl, Br, I, or F;

$X_3$, $X_4$, and $X_5$ are identical or different and represent H, Cl, Br, I, or F;

$X_6$ represents halogen, a group derived from the anion of an inorganic acid, OH, $OR_3$, $OCOR_4$, $NH_2$, $NHR_5$, or $NR_6R_7$, wherein each of $R_3$, $R_4$, $R_5$, $R_6$, and $R_7$ is an aromatic or aliphatic radical;

n is zero or an integer equal to or less than 5;

$R_1$ represents at least one element or moiety selected from hydrogen, OH, Cl, Br, I, F, alkyl and alkoxy radicals having from 1 to 6 carbon atoms, and phenyl and phenoxy radicals substituted by at least one group more deactivating than the $ACX_1X_2C_nX_3(X_4)_n(X_5)_n$ group; and $R_2$ represents an aliphatic or oromatic radical.

2. A process according to claim 1 wherein n=0 or 1 and $X_1$, $X_2$, and $X_3$ are identical.

3. A process according to claim 2 wherein $X_1$, $X_2$, and $X_3$ represent fluorine.

4. A process according to claim 1 wherein $R_2$ is a radical selected from the group consisting of alkyl, phenyl, alkylphenyl, phenylalkyl, and phenyl bearing at least one hologen, $NO_2$, CN, $NH_2$, or COOH substituent.

5. A process according to claim 1 wherein an amount of hydrofluoric acid is used such that the molar ratio of the hydrofluoric acid to the compound of formula II is between 5 and 50.

6. A process according to claim 1 wherein the hydrofluoric acid used is anhydrous hydrofluoric acid.

7. A process according to claim 1 wherein the compounds of formulas II and III are used in substantially equimolar amounts.

8. A process according to claim 1 wherein an amount of boron trifluoride is used such that the absolute pressure of $BF_3$ within the reaction vessel is from 6 to 20 bars.

9. A process according to claim 1 wherein the reaction temperature is from $-20°$ C. to $150°$ C.

* * * * *

UNITED STATES PATENT AND TRADEMARK OFFICE
CERTIFICATE OF CORRECTION

PATENT NO. : 4,446,078
DATED : May 1, 1984
INVENTOR(S) : Desbois

It is certified that error appears in the above—identified patent and that said Letters Patent is hereby corrected as shown below:

At column 4, line 20, "n=" should be --n=0--.

At column 4, line 52, "'" should be --4'--.

At column 10, line 55, "oromatic" should be --aromatic--.

At column 10, line 63, "hologen" should be --halogen--.

Signed and Sealed this

Twenty-sixth Day of March 1985

[SEAL]

Attest:

DONALD J. QUIGG

Attesting Officer         Acting Commissioner of Patents and Trademarks